USOO9816963B2

(12) United States Patent
Vetters et al.

(10) Patent No.: US 9,816,963 B2
(45) Date of Patent: Nov. 14, 2017

(54) HIGH PRESSURE COMPRESSOR THERMAL MANAGEMENT

(71) Applicants: Rolls-Royce North American Technologies, Inc., Indianapolis, IN (US); Rolls-Royce PLC, London (GB)

(72) Inventors: Daniel K. Vetters, Indianapolis, IN (US); Simon Mizzi, Derby (GB); Michael J. Agg, Bristol (GB)

(73) Assignees: Rolls-Royce North American Technologies, Inc., Indianapolis, IN (US); Rolls-Royce PLC (GB)

( * ) Notice: Subject to any disclaimer, the term of this patent is extended or adjusted under 35 U.S.C. 154(b) by 739 days.

(21) Appl. No.: 14/141,873

(22) Filed: Dec. 27, 2013

(65) Prior Publication Data
US 2014/0248122 A1 Sep. 4, 2014

Related U.S. Application Data

(60) Provisional application No. 61/771,689, filed on Mar. 1, 2013.

(51) Int. Cl.
*F01D 5/08* (2006.01)
*G01N 29/02* (2006.01)
(Continued)

(52) U.S. Cl.
CPC ............ *G01N 29/022* (2013.01); *F01D 5/082* (2013.01); *F02C 7/18* (2013.01); *F04D 19/02* (2013.01);
(Continued)

(58) Field of Classification Search
CPC ........ F01D 11/003; F01D 11/02; F01D 25/12; F01D 5/08; F01D 5/081; F01D 5/082; F01D 5/084; F01D 5/087; F01D 5/088; F05D 2220/3219; F05D 2260/22141; G01N 29/022; F04D 29/584; F04D 29/053; F02C 7/18
See application file for complete search history.

(56) References Cited

U.S. PATENT DOCUMENTS 2,973,938 A 3/1961 Alford
3,031,132 A 4/1962 Davies
(Continued)

FOREIGN PATENT DOCUMENTS

GB 2018362 A 10/1979

OTHER PUBLICATIONS

International Search Report for PCT/US2013/076533 mailed May 8, 2014.

*Primary Examiner* — Gregory Anderson
*Assistant Examiner* — Danielle M Christensen
(74) *Attorney, Agent, or Firm* — Fishman Stewart PLLC

(57) ABSTRACT

A gas turbine engine includes an inner shaft extending axially along the gas turbine engine, a plurality of disks extending radially inwardly and toward the inner shaft, at least one hole in at least one of the plurality of disks, and an obstruction positioned between the inner shaft and an end of the disk having the at least one hole, such that a bore flow that flows along an axial length of the inner shaft is obstructed from flowing along the shaft by the obstruction, and forced to flow radially outward from the obstruction, through the at least one hole, and radially inward toward the inner shaft.

20 Claims, 2 Drawing Sheets

(51) Int. Cl.
  *F04D 29/053* (2006.01)
  *F02C 7/18* (2006.01)
  *F04D 29/58* (2006.01)
  *F04D 19/02* (2006.01)

(52) U.S. Cl.
  CPC ......... *F04D 29/053* (2013.01); *F04D 29/584* (2013.01); *F05D 2240/12* (2013.01); *F05D 2250/232* (2013.01); *G01N 2291/0423* (2013.01); *Y02T 50/671* (2013.01); *Y02T 50/673* (2013.01); *Y02T 50/676* (2013.01); *Y10T 29/49229* (2015.01)

(56) References Cited

U.S. PATENT DOCUMENTS

| | | |
|---|---|---|
| 3,647,313 A | 3/1972 | Koff |
| 4,793,772 A | 12/1988 | Zaehring et al. |
| 4,795,307 A | 1/1989 | Liebl |
| 4,808,073 A | 2/1989 | Zaehring et al. |
| 4,920,741 A | 5/1990 | Liebl |
| 4,961,309 A | 10/1990 | Liebl |
| 5,271,711 A | 12/1993 | McGreehan et al. |
| 5,281,087 A | 1/1994 | Hines |
| 5,297,386 A | 3/1994 | Kervistin |
| 5,327,719 A | 7/1994 | Mazeaud et al. |
| 5,472,313 A | 12/1995 | Quinones et al. |
| 5,562,404 A | 10/1996 | Koff et al. |
| 6,035,627 A | 3/2000 | Liu |
| 6,267,553 B1 | 7/2001 | Burge |
| 6,361,277 B1 | 3/2002 | Bulman et al. |
| 6,672,072 B1 | 1/2004 | Giffin, III |
| 7,000,404 B2 | 2/2006 | Palmisano et al. |
| 7,278,821 B1 | 10/2007 | O'Reilly et al. |
| 7,841,187 B2 | 11/2010 | Behaghel et al. |
| 8,147,192 B2 | 4/2012 | Jones et al. |
| 2003/0133786 A1* | 7/2003 | Uematsu .............. F01D 5/084 415/115 |
| 2007/0189890 A1 | 8/2007 | Snowsill et al. |
| 2008/0063522 A1 | 3/2008 | Ashley |
| 2009/0044543 A1 | 2/2009 | Clemen et al. |
| 2011/0247344 A1 | 10/2011 | Glahn et al. |
| 2012/0003091 A1 | 1/2012 | Segovia |

* cited by examiner

HIGH PRESSURE COMPRESSOR THERMAL MANAGEMENT

CROSS-REFERENCE TO RELATED APPLICATIONS

This application claims priority to U.S. Provisional Patent Application No. 61/771,689, filed Mar. 1, 2013, the contents of which are hereby incorporated in their entirety.

FIELD OF TECHNOLOGY

A thermal management system is disclosed. The disclosed system pertains to the secondary flow system of a gas turbine engine and successfully managing the metal temperatures of a high-pressure compressor (HPC) in higher overall pressure ratio (OPR) gas turbine engines.

BACKGROUND

The trend in gas turbine engines is to improve engine efficiencies by increasing the OPR. This results in a relatively smaller core, and a higher bypass ratio. As OPR increases, the exit temperature of the high pressure compressor (HPC) correspondingly increases. Typically, in some known engines, areas of the engine that can limit OPR include temperatures that occur in spacer arm materials, rim and attachment materials, the cone shaft, and in the compressor-turbine (C-T) shaft. Known gas turbine engines also may include a secondary flow system that plumbs hot compressor air down the HPC cone shaft and along the C-T shaft. However, temperatures at the aft end of the compressor may be close to the compressor exit temperature. And, future engines being considered have compressor exit temperatures that may exceed material limits.

In some known systems, cooling air in the aft end is cooled to generate cooled cooling air (CCA) and a secondary flow system, and there have been approaches for CCA in which the drive cone and C-T shaft are exposed to CCA. However, CCA systems typically focus on managing temperatures within the hot section of the engine (NGV's, high-pressure turbines (HPTs), other turbines, turbine casings, etc.). And, secondary flow circuits typically transfer flow between the gas path and the bores and the flow is typically taken in only one direction.

As a result there is a need to thermally manage the aft end of the HPC to maintain metal temperatures within the temperature range for which materials are capable. By having an effective thermal management system, a higher OPR cycle can be enabled resulting in improved specific fuel consumption (SFC) and less fuel burn per aircraft mission.

BRIEF DESCRIPTION OF THE DRAWINGS

While the claims are not limited to a specific illustration, an appreciation of the various aspects is best gained through a discussion of various examples thereof Referring now to the drawings, exemplary illustrations are shown in detail. Although the drawings represent the illustrations, the drawings are not necessarily to scale and certain features may be exaggerated to better illustrate and explain an innovative aspect of an example. Further, the exemplary illustrations described herein are not intended to be exhaustive or otherwise limiting or restricted to the precise form and configuration shown in the drawings and disclosed in the following detailed description. Exemplary illustrations are described in detail by referring to the drawings as follows:

DETAILED DESCRIPTION

The disclosed system has advantages over other known systems due to its simplicity, resulting in lower cost, weight, complexity, and risk. The disclosed system manages the metal temperatures at the aft end of a high pressure (HP) compressor for a high overall pressure ratio (OPR) gas turbine engine.

Figure 1:
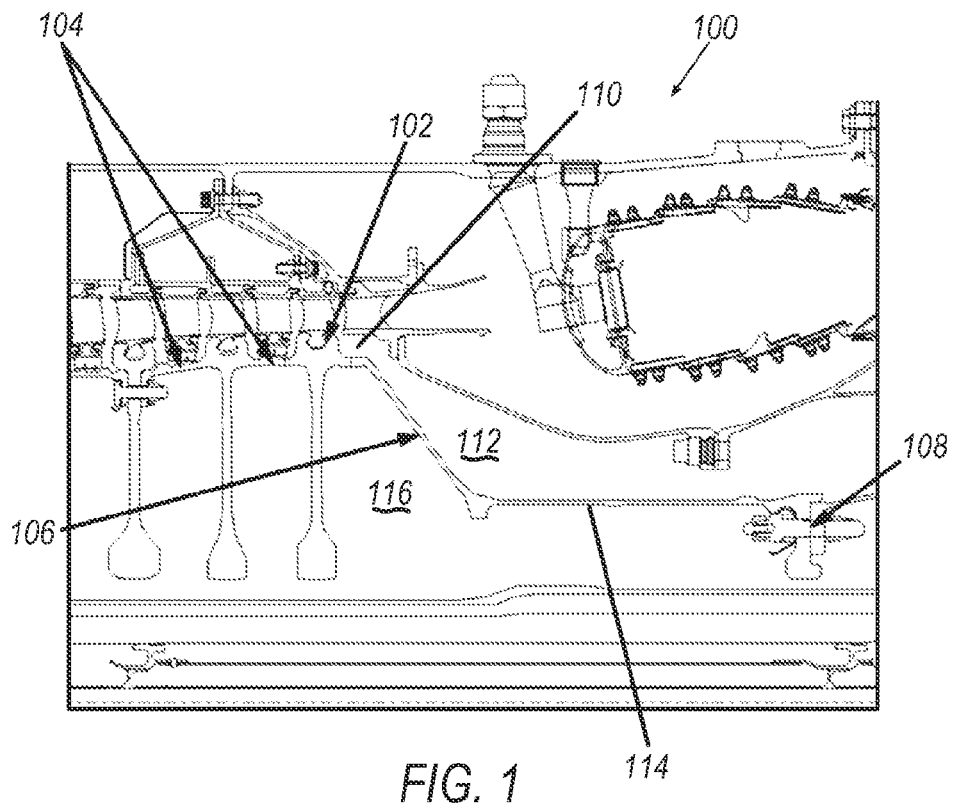
FIG. 1 illustrates an aft end of an axial compressor that incorporates embodiments of the disclosure.

FIG. 1 illustrates an aft end 100 of an axial compressor that incorporates embodiments of the disclosure. Illustrated areas include aft rim and attachment of the HPC 102, spacer arms 104 between the last few stages of the HPC, an HPC drive cone 106, and a C-T shaft bolted joint 108. A secondary flow system plumbs hot compressor air from the compressor exit 110 and down the HPC cone shaft and along a radially external region 112 of a C-T shaft 114. However, temperatures at the aft end of the compressor, as stated, may be close to the compressor exit temperature. Cooler air from the intermediate pressure compressor (IPC), may be provided in a region 116 that is radially internal to the C-T shaft 114. Temperatures in at least external region 112 may approach, and in some future engine designs, have compressor exit temperatures that may exceed material limits.

Figure 2:
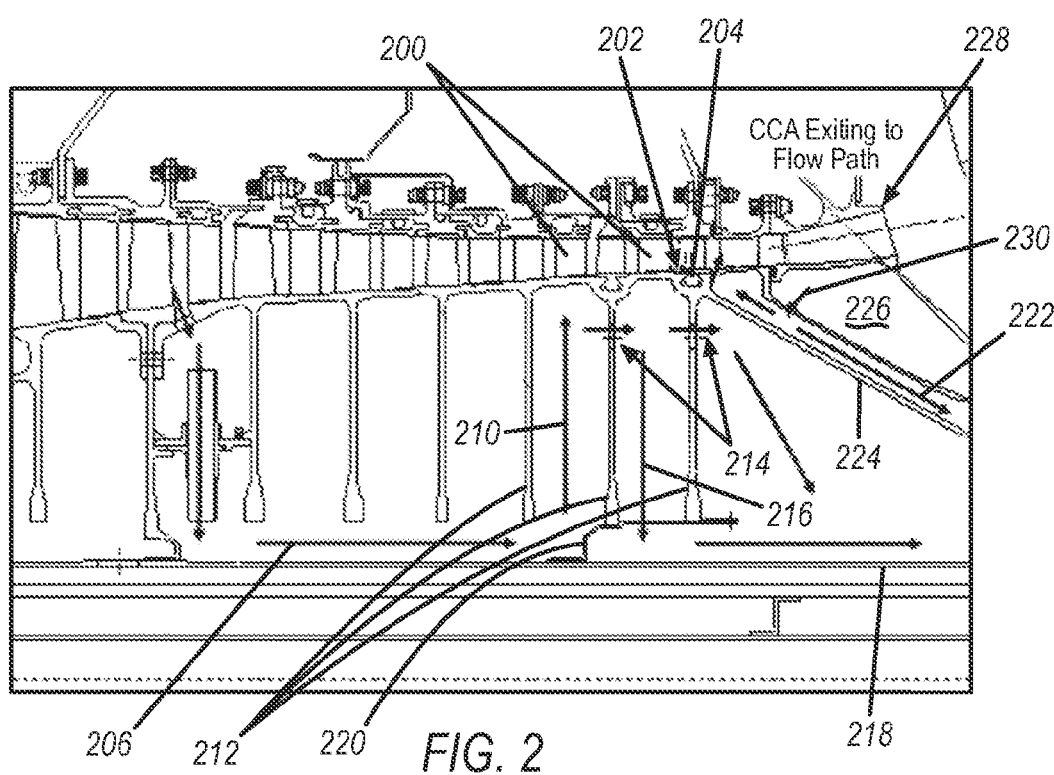
FIG. 2 illustrates various elements that each address and enhance thermal management within an aft end of a turbine engine.

Thus, referring to FIG. 2, to manage temperatures in aft end 100 as shown in FIG. 1, a system is disclosed with various elements that each address and enhance thermal management within aft end 100. The system includes:

Cantilever vanes 200 for the last few stages of HPC stators. Vanes 200 are included that eliminate the windage associated with shrouded compressor vanes. The inherent windage in the vane wells adds temperature to the spacer arms. The added temperature can drive the spacer arm metal temperatures above the HPC exit temperature. Thus, by eliminating the vane wells, the windage is eliminated and the spacer arms deal with the gas path temperatures (which is inherently lower than the compressor exit temperature).

Cooled Cooling Air (CCA) exits to the flowpath at the aft face 202 of the last stage of the HPC compressor. Traditionally, engines allow the hot air exiting the compressor to flow out of the flowpath through the gap between the last stage of the HPC and the outlet guide vane (OGV) (shown generally as element 204). There are often flow discouragers or seals in this location, but typically, the direction of flow is from the flowpath into the internal cavities. This results in the aft face of the last stage HPC rim being passed by hot, compressor exit temperature air. As compressor discharge temperature (CDT) goes up with OPR, the result of the traditional design can be excessive temperature at the aft face of the last stage HPC rim. By changing the secondary flow system in conjunction with a CCA system, the direction of flow after the HPC can be changed to be outward, into the flowpath from the internal cavities using cool air. The result is the aft face of the last stage rim being passed with cool air and acceptable metal temperatures.

Thus, at general location 204 and according to one example, CCA is plumbed through the last stage attachment to exit to the flowpath forward of the last stage of HPC. The issue being addressed is the conduction of the flowpath temperature from the blades (acting as large fins) into the rim via contact at the attachment slot(s). This conduction path results in high temperatures at the contact points, even if the temperatures elsewhere are addressed. Therefore temperatures at this location are managed. By routing some of the air exiting to the flowpath aft of the HPC to flow through the last stage attachment, the temperatures in the attachment area can be managed. The CCA is channeled between the platform and rim OD to the circumferential attachment slot. The air then flows through metering holes in the skirts of the blades' circumferential attachment to once again flow between the blade platform and the rim OD before exiting to the flowpath just forward of the last stage blade.

Additionally, still referring to FIG. 2, HPC bore flow 206 is re-routed (via an obstruction, in the example illustrated) to flow outward 210 between HPC discs 212, through holes 214 in the HPC (diaphragms or webs), and back inboard 216 to continue the typical flow along inner shaft (or flow divider/heat shield) 218 towards the aft of the engine. According to the illustrated example, the obstruction that causes bore flow 206 to be re-routed is a radially extending obstruction 220, positioned to obstruct bore flow 206 and cause the bore flow 206 to re-direct radially outward 210, pass through holes 214, and then pass radially inward 216. The purpose of this is to force the bore flow against the inner surface of the aft spacer arm(s) with a mismatched swirl. This results in efficient heat transfer from the spacer arms as the bore flow scrubs the inner surface. This results in acceptable metal temperatures in the spacer arm(s).

Furthermore, CCA flows 222 down the HPC drive cone 224 and along the C-T shaft (element 114 of FIG. 1), towards the aft of the engine. This creates a cooler environment for these areas, thereby managing the metal temperatures in the drive cone and the C-T shaft bolted joint (element 108 of FIG. 1).

Cantilever vanes are often avoided due to an expected decrease in aero performance. Cantilever vanes with large tip clearances have been known to have poorer performance compared to shrouded vanes. But, cantilever vanes with well controlled tip clearances have the same and sometimes better performance than shrouded vanes. One deciding factor is how tightly the tip clearance can be controlled.

High OPR engines have challenges with respect to the blade height on the last stage of the HPC. As a result, the last stage blade spans tend to be as short as possible. This results in the aft end of the HPC being very sensitive to blade tip clearances. Therefore, the aft end of the compressor can be designed and managed to ensure tight running clearances at the blade tips under both operating and transient conditions. If this is not accomplished then performance penalties may result. A natural consequence of managing the blade tip clearances inherently manages cantilever vane tip clearances at the aft end of the compressor as well. Thus, cantilever vanes at the aft end of the compressor can improve performance and generally do not require additional attention to tip clearance management, since tip clearances are already being managed for the blades.

As stated, high OPR engines often have HPC exit temperatures higher than the disc materials can handle. As a result, Cooled Cooling Air (CCA) provides cooling, according to one example. A source of air with adequate pressure, at location 226, forces flow through the proposed system is air taken after a diffuser 228. At this location the kinetic energy of the air at the aft end of the HPC has been converted to an increase in static pressure such that there is adequate pressure to drive flow outward into the gas path. The air in this location 226 is roughly the same temperature as the air at the HPC exit. As such, the air available for cooling is above the material temperature capability. Thus, a small portion of this air is cooled, using a heat exchanger (not shown) to be used in the thermal management system described. Air is taken aft of the diffuser 228 (so it has adequate pressure). This air then passes through a heat exchanger and is cooled, as is commonly known. According to an example of the disclosure, the cooled air is then introduced, at location 230, proximate the aft rim of the HPC or along the drive cone to flow forward for thermal management of the HPC rim and attachment and rearward for thermal management of the drive cone and C-T shaft bolted joint. By using CCA, the available source of cooling air has both adequate pressure and low enough temperature to create a successful thermal management system.

The example shown has a flow obstruction or discourager at the aft rim of the HPC that also acts to introduce the CCA flow into the gas path with the least amount of disruption possible. If too much flow is introduced or if it is introduced poorly, significant performance losses could result. Therefore the geometry in this area is important. Overall, the flow into the gas path should be minimized for performance reasons, but 0.1% to 0.2% of flow would not be expected to significantly impact performance based on the recirculation flows typically present with shrouded vanes. This creates a soft limit for how much flow can be introduced into the gas path at a given location. If metal temperatures are not achieved with flows close to this range, then according to another example, another design option is to further reduce the temperature of the CCA.

To avoid flowing too much air into the gas path during key performance points, the flow could be allowed to reverse slightly during short transients and/or during lower temperature operating points when the HPC exit temperature is below the allowable temperatures of the materials, providing a reasonable trade to avoid spoiling the flow in the main gas path during high temperature operating conditions.

The disclosed example that reroutes the bore flow outward between discs, through holes in disc webs (diaphragms), and inward to continue flowing aft along the bore is one portion of the overall disclosed thermal management system. Current low to mid OPR engines can still have issues with metal temperatures at the aft end of the HPC. Particularly when using traditional shrouded vanes, the windage in the vane wells can significantly heat the air outboard of the spacer arms, resulting in high spacer arm temperatures. The rerouting (or hijacking) of the bore flow to pass along the inner surface of the spacer arms and to flow through holes in the disc webs can be a very useful method of managing temperatures in the spacer arms. It can also help in managing thermal gradients during transients in the discs through which the bore flow is plumbed along and through. As such, the disclosed example of rerouting airflow can be a useful tool on its own for improving the life and/or reducing weight of the discs at the aft end of the compressor on existing engines, independent of the full thermal management system for high OPR engines.

One important aspect of the disclosed example is the increased heat transfer that results from the air swirling at a different speed than the spacer arms. For a rotating fluid that approaches solid body type rotation (forced vortex) it can be shown that as the air moves outward 210 between the discs 212, the linear velocity of the disc is increasing linearly with radius. Conversely if air 210 rotates freely (free vortex) the linear velocity decreases if the radius increases. Given that the discs are a solid body an air motion that approaches a free vortex type motion would yield the largest difference in linear velocity and as a consequence a much more enhanced heat transfer.

Another effect of the re-routing concept is to also reduce thermal gradients in the discs during transients. The air passing the sides of the discs 212 as it flows outward 210 and inward 216, along with the air flowing through the holes 214 in the webs (diaphragms), will enhance the heat transfer from the disc to the surrounding air. As a result, the bore and web will heat up faster during accelerations and will cool down faster during decelerations. This will reduce thermal gradients, resulting in lower thermal stress. Depending on what is sizing the wheel, this could lead to a reduction in size and weight for the disc, or in the alternative, could lead to longer life.

Additionally, as shown and discussed, a bore seal or flow discourager 220 is used beneath the disc that is the dividing line between the outward flowing disc(s) and the inward flowing disc(s). The discourager need not be a completely air-tight seal. However, some flow restriction is included to encourage the air to flow through the re-routed circuit (outward 210, through holes 214, and inward 216).

To enable the bore flow rerouting concept, the downstream recipients of the bore flow will typically include an increase in air temperature. The amount of temperature increase can be manipulated for the best trade between HPC cooling and thermal management, and components using the bore flow downstream of the HPC. Less heat transfer adds less heat into the air, but will also take less heat out of the HPC metal. An appropriate balance is thus maintained.

Figure 4:
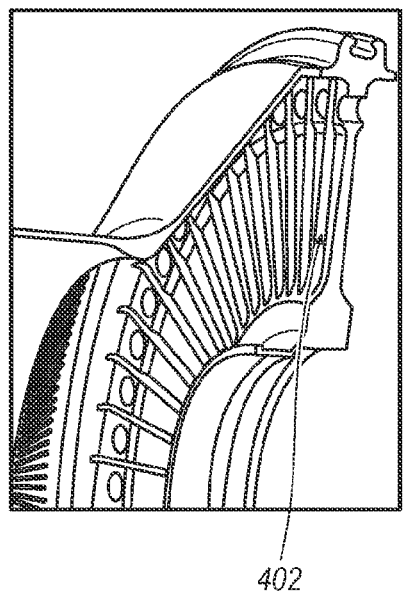
FIG. 4 shows a 3D representation of one bore flow circuit example.
Figure 4:
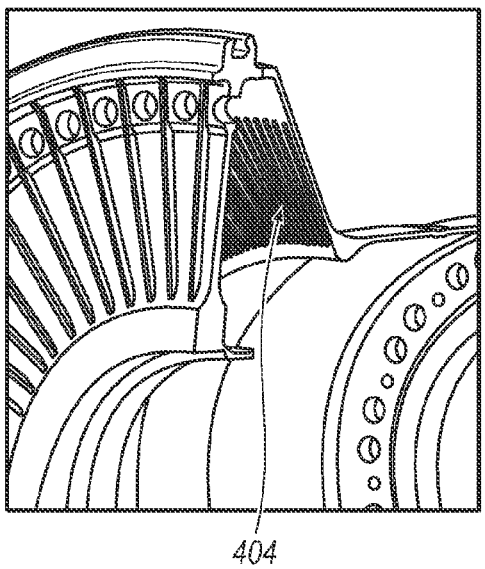

The re-routing concept could result in a pressure drop in the bore flow as well. Fins or paddles 402 could be added to the sides of the discs through which the air moves outward as shown in FIG. 4. These would be designed to pump up the air (approach a forced vortex type motion—described above—as it moves outward between the discs. This could be used to counter any subsequent pressure drops through the re-routed system. However, besides adding cost, weight, and complexity to the discs, the system may experience an increase in air temperature and a decrease in the difference in swirl at the inner surface of the spacer arms (poorer heat transfer) since the rotational air motion approaches a forced vortex type of motion. As such, it may be desirable to avoid additional pumping of the bore flow. If little or no pressure drop can be tolerated, this is an additional example which could address the sensitivity to bore flow pressure.

An alternate solution to the pressure drop solution may be to add fins, paddles, etc. to the inward flowing disc 404 (or drive cone) faces to force the air inward without as much pressure loss. A first course of action may be to minimize the pressure drop through the circuit. One method of accomplishing this may be to allow the flow to return to the bore via more than one disc cavity, which may result in a reduced overall pressure drop. Also, flow down the drive cone and aft along the C-T shaft could be used independent of the rest to specifically manage the drive cone, C-T shaft, and C-T shaft bolted joint temperatures. As discussed, by thermally managing the aft end of the HPC, OPR can be increased, resulting in a smaller core, higher bypass ratios, and better efficiencies—which can lead to less fuel burn for the end customer.

Alternative concepts such as feeding CCA through the shrouded vanes may add complexity and may impact the aerodynamics of the vanes since they may be thicker to allow the air flow passages. Adding spacer arm platforms (similar to the blade attachments and platforms but without a blade attached) could be used to isolate the spacer arms from the gas path and/or to provide a flow passage for CCA. However, such an approach may add weight and complexity along with making the cantilever vane tip clearances much more difficult to maintain.

Current/known engine secondary flow systems have a ratio of bore flow to compressor exit air flowing around the compressor cone and C-T shaft on the order of 2:1, as one example. A low level of heat transfer is currently being achieved from the bore fluid, indicating natural convection behavior in board of the compressor cone, while forced convection (higher level of heat transfer) prevails outboard of the cone. Moreover, current predictions indicate that the compressor exit air loses approximately 11 K, suggesting that increasing heat transfer in board of the compressor would provide a cooler HP6 air (in region 222) up the turbine disc diaphragm. The compressor exit air continues on to immerse the front diaphragm of the HPT, which is sometimes the hottest region on the disc and therefore may be a key life-limiting feature on the disc, in known designs.

This indicates that a flow with relatively high cooling capacity may not be efficiently made use of as a heat sink that, which could potentially procure a substantial benefit to both the thermal environment and mechanical life of the HP turbine disc. Therefore the disclosed system further exploits this heat transfer mechanism between the two air systems by enhancing the heat transfer on the inboard side of the compressor cone that is immersed in bore flow, which may lead to a cooler compressor exit air and a hotter bore flow, and reduced metal temperatures on the front diaphragm and reduced thermal gradients on the HPT disc.

Thus, CCA introduced at the top of the drive cone and flowing aft along the drive cone and along the C-T shaft readily manages the metal temperatures in these areas. Flowing CCA along the drive cone and C-T shaft in this manner manages the temperatures in these areas independent of the thermal management and/or metal temperatures at the HPC rim, attachment, and spacer arms. Therefore, this is one concept that may be applied independent of the others to manage temperatures in these areas.

In summary, a full thermal management system enables OPR to be increased higher than previously possible. This enables a reduction in core size, increasing bypass ratio (without increasing fan diameter) and improving efficiency. Ultimately this results in less fuel burn in an aircraft for a given mission.

While the full system enables high OPR engines, several of the concepts could be used independent of the others to address specific thermal management issues in today's engines. For instance, using cantilever vanes to specifically eliminate vane well heating as a means to enable higher OPR engines may be used on its own and independent of other disclosed elements herein. That is, cantilever vanes could be used independent of the rest if the system has vane well heating issues.

Or, re-routing of the bore flow to thermally manage the spacer arms and the discs at the aft end of the HPC could be used independent of other disclosed elements disclosed herein, such as in an engine application in which peak metal temperatures are challenged in the spacer arms or with transient thermal gradients in the discs. As discussed previously, routing of CCA down the drive cone and after along the C-T shaft can be used independent of the rest to thermally manage the temperatures in the drive cone, C-T shaft, and C-T bolted joint. However, the full system enables higher OPR cycles to be pursued that were previously not feasible. And it does this in a very simple way that avoids cost, complexity, and weight.

There are alternative variations on the details in each of the system components. Variations include but are not limited to:

1) Cantilever vanes are sometimes mated against a bare metal spacer arm. Other times a hard coat is placed on the outside of the rotor spacer arms so that in the case of contact, the vane tip will wear away rather than the spacer arm. This concept could be used either way.
2) One improved situation would be if a hard coating is applied to the spacer arms that also acted as a thermal barrier coating (TBC). This would be accomplished if the hard coating has a thermal conductivity lower than the base metal. In this way, the hard coating would serve a dual purpose: it would protect against rubbing and would also reduce the heat being transferred into the metal, thereby aiding in thermal management.

This system could be applied without the cantilever vanes and could be successful if the rerouting of the bore flow to pass along the inside of the spacer arms was adequate to maintain appropriate spacer arm temperatures, even in the presence of vane well heating.

Instead of feeding CCA to the circumferential attachment slot between the blade platform and the outer diameter (OD) of the rim, drillings could be used on the back face of the last stage of HPC to conduct CCA through the rim to the circumferential blade attachment slot. This would typically be avoided to avoid the added cost and the stress concentrating aspect of such drillings, but this could be done if needed or desired.

The figures shown depict the last stage of HPC blades to have circumferential attachments. This concept would also work with axial (or helical or curved) dovetail attachment slots. With such an arrangement, features would be in place to block flow through the attachment slots (via a retaining plate, blind attachment slots, etc.) such that flow metering holes could be used to control the amount of leakage through the attachment slots.

One example has a flow discourager at the aft rim that also acts to introduce the CCA flow into the gas path with the least amount of disruption possible. Too much flow outward could result in spoiling the flow in the main gas path and significant performance losses. Too much inflow during transients could also lead to metal temperatures above the allowable metal temperatures. Another example to address this would be to replace the aft rim flow discourager with an actual seal. One embodiment would be a labyrinth seal, but other seal types could also be used. By placing a seal in this location, the flow to and from the gas path could be controlled much better.

If the aft rim flow discourager were replaced with a seal arrangement between the aft rim of the HPC rotor and the static OGV or diffuser, then one example would be to use circumferential blade attachment on the last stage of the HPC. This provides an axisymmetric rim to the OD of the disc on which features for a seal could be attached. In such an arrangement, flow out of the attachment slot could be out one direction only (opposite of the attachment skirt direction) or flow could be in two directions (also through flow holes in the attachment skirts).

Several varying embodiments for the bore flow rerouting may also be considered, such as flowing outward and inward through a single or multiple cavities, adding fins or paddles to pump air outward to regain pressure loss, etc. The means of blocking off the bore to encourage the flow to take the new, alternate route could be accomplished many different ways, one of which is shown in FIG. 2.

Figure 3:
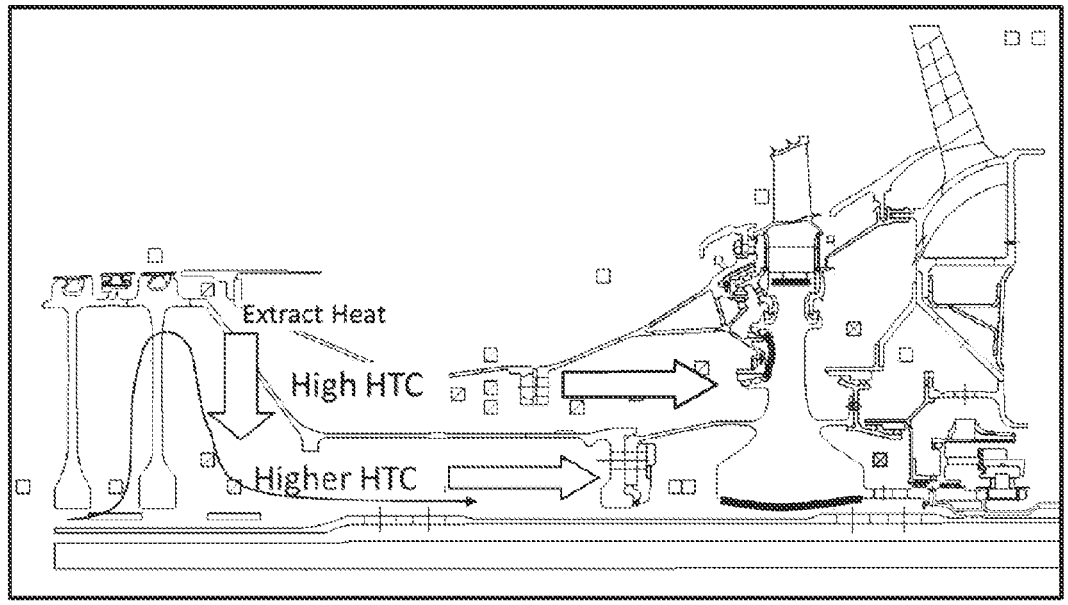
FIG. 3 illustrates an exemplary physical concept and purpose behind the bore flow re-routing.

Referring to FIG. 3, the combined cantilever arrangement of the stator vanes, cooled cooling air, the revisited pre-swirl last stage off-take and re-routed bore flow of the secondary air system have a combined benefit of approximately 30K (° C.) or greater in temperature reduction HPC inter-stage rims when compared to conventional cooling systems currently in place. The temperature reduction extends the applicability of current materials used in HPC architectures ensuring mechanical integrity and extending cyclic life. Additionally, the system also ensures minimal pressure loss across the cooling secondary air system, minimizing the impact on the engine performance.

FIG. 4 provides a 3D representation of one bore flow circuit example. The flow that is rerouted around the last stage HPC disc can be metered according to the heat exchange requirement by varying the seal clearance of the newly introduced seal. In one example, having 90% of the flow rerouted, the level of heat transfer inboard of the cone is comparable to that outboard and the following benefits are expected:

A 5% decrease of the turbine cooling air flowing on the outboard side of the C-T shaft (assuming compressor exit temperature cooling air). This would translate to a 5% decrease of HP turbine disc diaphragm temperatures and a 1% increase of disc rim temperatures (alternatively, this could be used to reduce the amount of parasitic cooling air flow to the turbine for the same life). A 3% increase of secondary bore flow temperature. A 10% reduction in rim thermal gradients and stresses. A 25% reduction in bore thermal gradients and stresses.

In summary, cantilever vanes have been used before, but not for the purpose disclosed of managing HPC rotor spacer arm metal temperatures. Cooled cooling air (CCA) can be used in conjunction with the rest of the system to manage metal temperatures at the aft end of the HPC. The rerouting concept purposefully takes flow both ways to create a differential swirl at the inner surface of the spacer arms to accentuate the heat transfer, specifically to manage the metal temperatures in the spacer arms The illustrated examples show a system that works in harmony with the other concepts to not only manage drive cone and CT shaft temperatures but also sets the stage for thermal management of the HPC rim and attachment by creating an environment with high pressure CCA on the aft face of the HPC. By applying CCA in this manner, not only are the drive cone and C-T shaft temperatures managed, but the HPC metal temperatures are managed as well.

It will be appreciated that the aforementioned method and devices may be modified to have some components and steps removed, or may have additional components and steps added, all of which are deemed to be within the spirit of the present disclosure. Even though the present disclosure has been described in detail with reference to specific embodiments, it will be appreciated that the various modifications and changes can be made to these embodiments without departing from the scope of the present disclosure as set forth in the claims. The specification and the drawings are to be regarded as an illustrative thought instead of merely restrictive thought.

What is claimed is:
1. A gas turbine engine, comprising:
an inner shaft extending axially along the gas turbine engine;

a first disk and a second disk extending radially inwardly and toward the inner shaft, the first and second disks located adjacent to one another and each having a center bore aperture;

a first hole in the first disk and a second hole in the second disk; and an obstruction positioned in the center bore aperture of the first disk, such that a bore flow that flows along an axial length of the inner shaft is obstructed from flowing along the shaft by the obstruction, and flows radially outward from the obstruction, through the first hole, radially inward toward the inner shaft, and through the center bore aperture of the second disk, the obstruction extending through the center bore apertures of the first and second disk.

2. The gas turbine engine of claim 1, further comprising a cone shaft aft of the plurality of disks, and a cavity formed in part by an external portion of the cone shaft, wherein-air is received aft of a diffuser, flows forward, opposite an aft end of the gas turbine, and into the cavity, and split within the cavity such that some of the air flows forward in the cavity to exit at an aft face of the gas turbine engine.

3. The gas turbine engine of claim 2, wherein, at the split within the cavity, some of the air flows down the cone shaft toward the aft end of the gas turbine and along an outer surface of a C-T bolted joint of the gas turbine engine.

4. The gas turbine engine of claim 3, wherein a second cavity is formed in part by the second disk, an inner surface of the C-T shaft, and the inner shaft, such that some of the bore flow obstructed from flowing along the shaft flows through the second hole in the second disk, into the second cavity, and rejoins with the bore flow aft of the obstruction that passed through the first hole and not through the second hole.

5. The gas turbine engine of claim 4, wherein the external portion of the cone shaft is one surface of the cone shaft, and the second cavity is formed in part by a second surface of the cone shaft that is opposite the one surface of the cone shaft.

6. The gas turbine engine of claim 1, wherein the bore flow that flows radially outward flows along a first surface of the first disk, and flows radially inward along a second surface, opposite the first surface, of the first disk.

7. The gas turbine engine of claim 1, wherein the obstruction is coupled to an outer surface of the inner shaft and the end of the first disk.

8. A method of assembling a gas turbine engine, comprising:

positioning an inner shaft to extend along a rotational axis of the gas turbine engine;

positioning disks to extend radially inward toward the inner shaft;

forming a first hole in a first of the disks and a second hole in a second of the disks that is adjacent to the first of the disks;

forming a center bore aperture in each of the first and second disks; and positioning an obstruction in the center bore aperture of the first of the disks, such that a bore flow that flows along the rotational axis and along the inner shaft is obstructed from flowing along the shaft by the obstruction, and flows radially outward from the obstruction, through the first hole, radially inward toward the inner shaft, and through the center bore aperture of the second disk, the obstruction extending through the center bore apertures of the first and second disk.

9. The method of claim 8, further comprising positioning a cone shaft aft of the disks to form a cavity in part by an external portion of the cone shaft, wherein air is received aft of a diffuser, flows forward, opposite an aft end of the gas turbine, into the cavity, and split within the cavity such that some of the air flows forward in the cavity to exit at an aft face of the gas turbine engine.

10. The method of claim 9, wherein, at the split within the cavity, some of the air flows down the cone shaft toward the aft end of the gas turbine and along an outer surface of a compressor-turbine (C-T) shaft and to a C-T bolted joint of the gas turbine engine.

11. The method of claim 10, wherein a second cavity is formed in part by the second of the disks, an inner surface of the C-T shaft, and the inner shaft, such that some of the bore flow obstructed from flowing along the shaft flows through the second hole in the second of the disks, into the second cavity, and rejoins with the bore flow aft of the obstruction that passed through the first hole and not through the second hole.

12. The method of claim 11, wherein the external portion of the cone shaft is one surface of the cone shaft, and the second cavity is formed in part by a second surface of the cone shaft that is opposite the one surface of the cone shaft.

13. The method of claim 8, wherein the bore flow that flows radially outward flows along a first surface of the first of the disks and flows radially inward along a second surface, opposite the first surface, of the first of the disks.

14. The method of claim 8, further comprising coupling the obstruction to an outer surface of the inner shaft and the end of the first of the disks.

15. A method of cooling a gas turbine engine, comprising:

directing a bore flow to flow along a rotational axis of an inner shaft of the gas turbine engine and to an obstruction along the inner shaft that obstructs the bore flow from flowing along the shaft, wherein the bore flow is forced radially outward from the obstruction, through a first hole in a first disk and a second hole in a second disk that is adjacent to the first disk, and radially inward toward the inner shaft and through a center bore aperture of the second disk, the obstruction extending through the center bore aperture of the second disk and extending through a center bore aperture of the first disk, and wherein each disk extends radially inward toward the inner shaft.

16. The method of claim 15, further comprising receiving air aft of a diffuser, flowing the air in a forward direction of the gas turbine engine that is opposite an aft end of the gas turbine, into a cavity, and splitting the air within the cavity such that some of the air flows forward in the cavity to exit at an aft face of the gas turbine engine, wherein the cavity is formed in part by an external portion of the cone shaft.

17. The method of claim 16, wherein, at the split within the cavity, the method further comprises passing some of the air down the cone shaft toward the aft end of the gas turbine and along an outer surface of a compressor-turbine (C-T) shaft and to a C-T bolted joint of the gas turbine engine.

18. The method of claim 17, further comprising flowing some of the bore flow that is obstructed through the second hole, into a second cavity that is formed in part by the second of the disks, an inner surface of the C-T shaft, and the inner shaft, and rejoining with the bore flow aft of the obstruction that passed through the first hole and not through the second hole.

19. The method of claim 18, wherein the external portion of the cone shaft is one surface of the cone shaft, and the second cavity is formed in part by a second surface of the cone shaft that is opposite the one surface of the cone shaft.

20. The method of claim 15, wherein the bore flow that is forced to flow radially outward flows along a first surface of the first disk, and flows radially inward along a second surface, opposite the first surface, of the first disk.

* * * * *